United States Patent [19]

Huffman

[11] Patent Number: 4,494,934
[45] Date of Patent: Jan. 22, 1985

[54] DENTAL MODEL BASE
[75] Inventor: Ronald E. Huffman, Tucson, Ariz.
[73] Assignee: KV33 Corporation, Tucson, Ariz.
[21] Appl. No.: 323,735
[22] Filed: Nov. 23, 1981

Related U.S. Application Data

[62] Division of Ser. No. 230,330, Feb. 2, 1981, Pat. No. 4,378,979.

[51] Int. Cl.³ ........................ A61C 11/00; B29C 1/16
[52] U.S. Cl. ...................................... 433/213; 249/54
[58] Field of Search ...................... 249/54; 433/60, 213

[56] References Cited

U.S. PATENT DOCUMENTS

| 1,599,487 | 9/1926 | Porter | 249/54 |
| 2,266,434 | 12/1941 | Morrison | 433/60 |
| 2,841,871 | 7/1958 | Miller | 433/60 |
| 3,226,827 | 1/1966 | Spalten | 249/54 |
| 3,498,580 | 3/1970 | Wilson | 249/54 |
| 3,838,187 | 9/1974 | Thomas | 264/17 |
| 4,359,435 | 11/1982 | Kogure | 264/17 |

FOREIGN PATENT DOCUMENTS

| 2835094 | 2/1980 | Fed. Rep. of Germany | 433/60 |
| 23899 | 8/1935 | United Kingdom | 433/60 |

Primary Examiner—Willard E. Hoag
Attorney, Agent, or Firm—Cahill, Sutton & Thomas

[57] ABSTRACT

A preformed dental model base, for use with an articulator, characterized by a flat bottom surface and a flat elevated upper platform surface spaced above other upper portions of the base.

5 Claims, 17 Drawing Figures

U.S. Patent  Jan. 22, 1985  Sheet 1 of 3  4,494,934
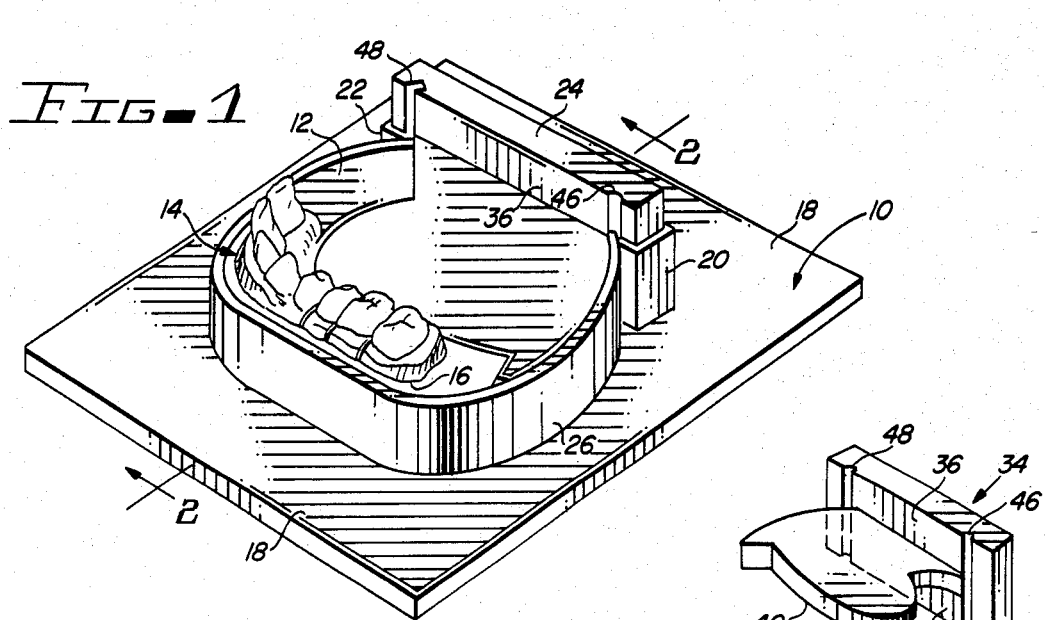
FIG-1
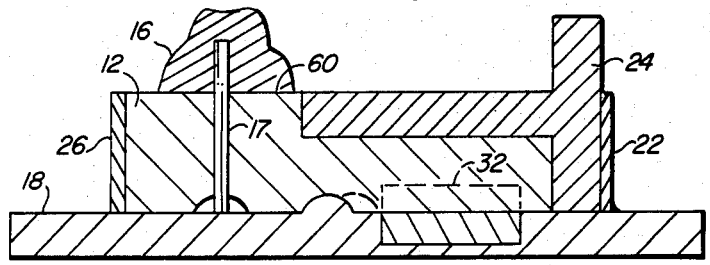
FIG-2
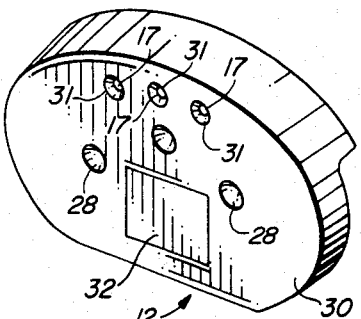
FIG-4
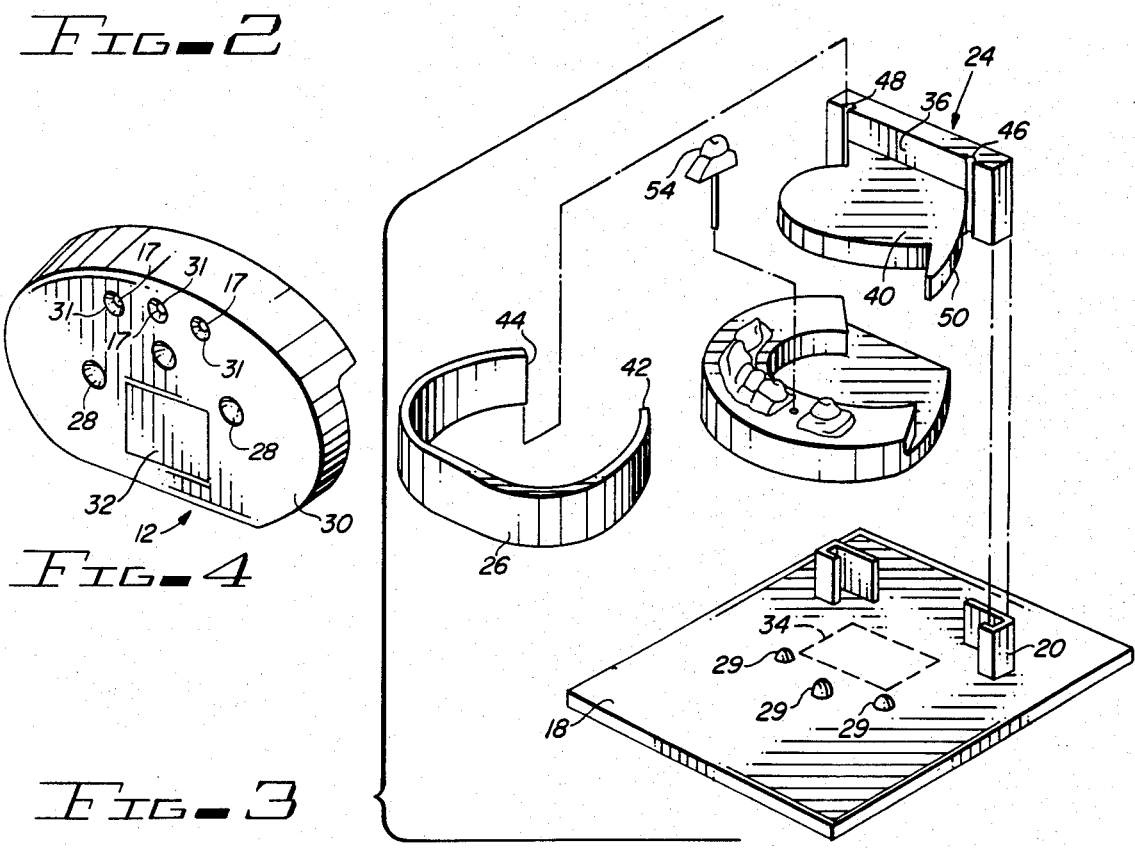
FIG-5
FIG-3

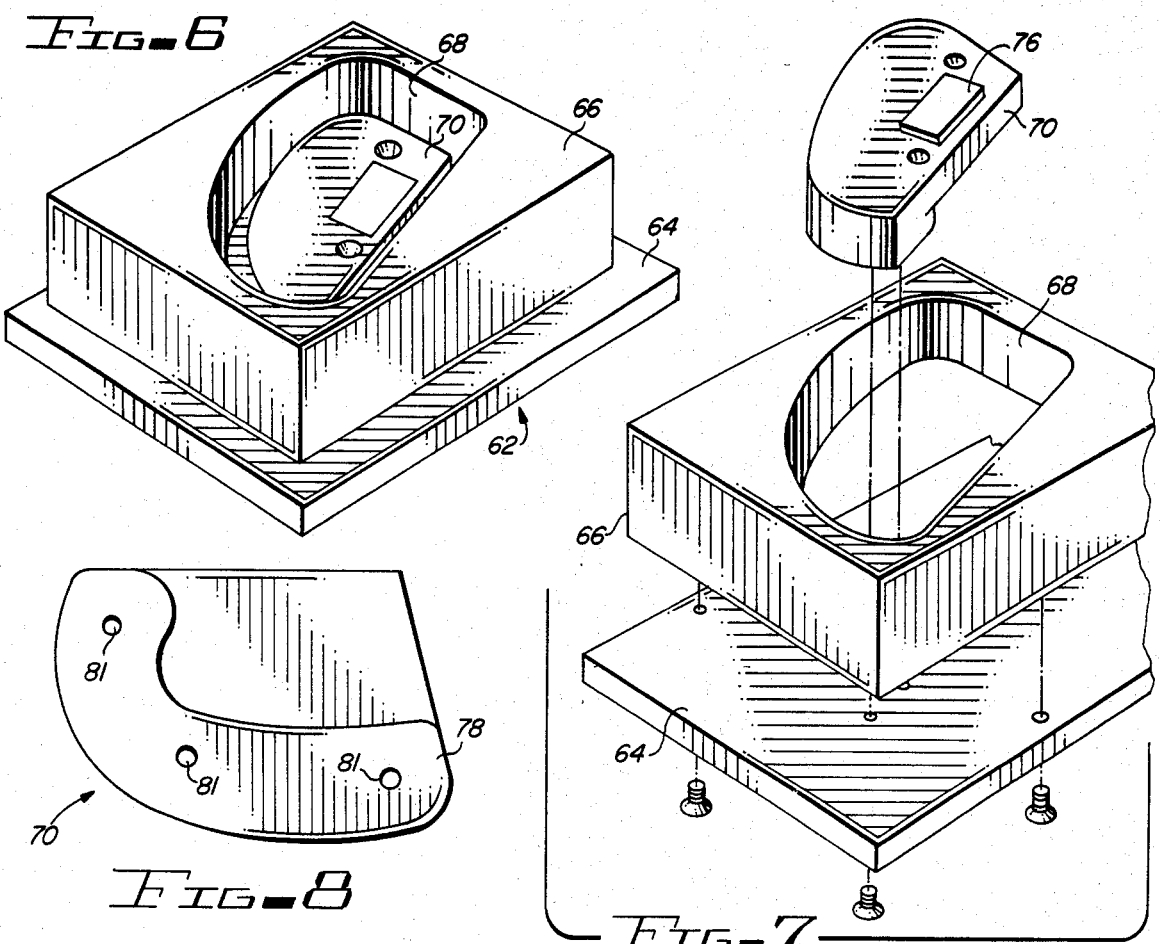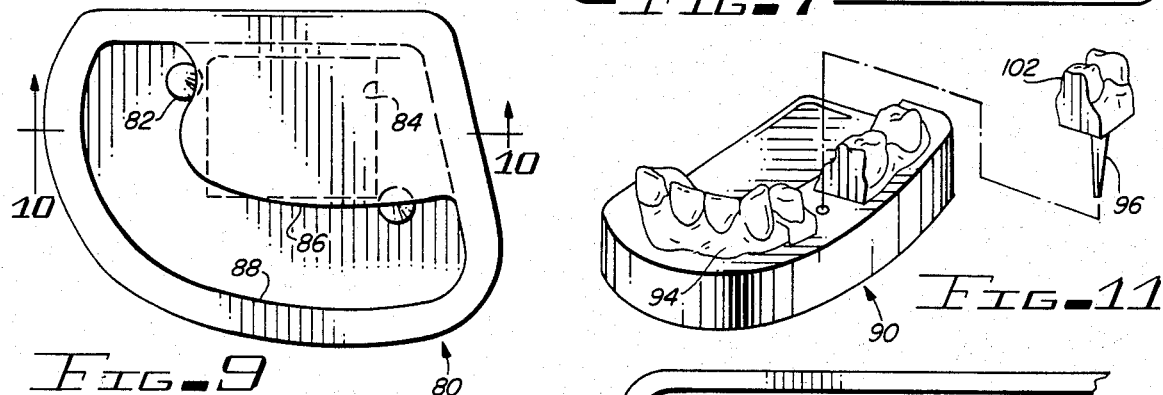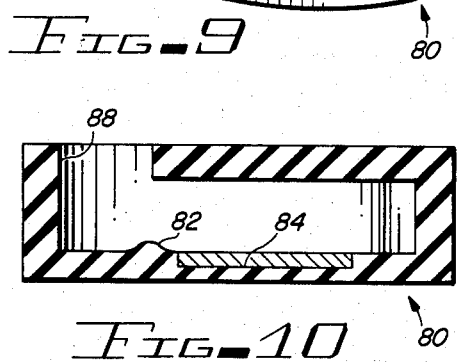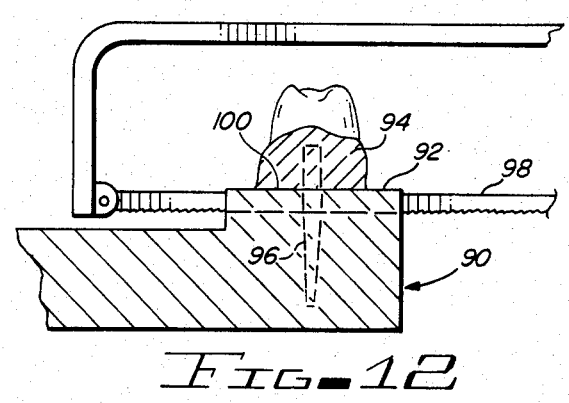

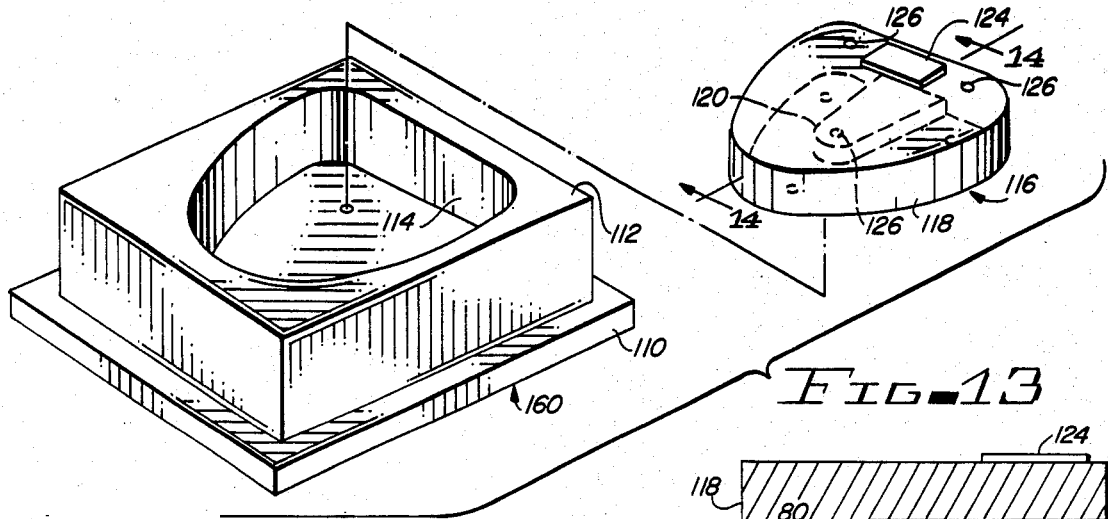
FIG-13
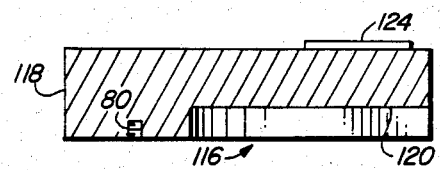
FIG-14
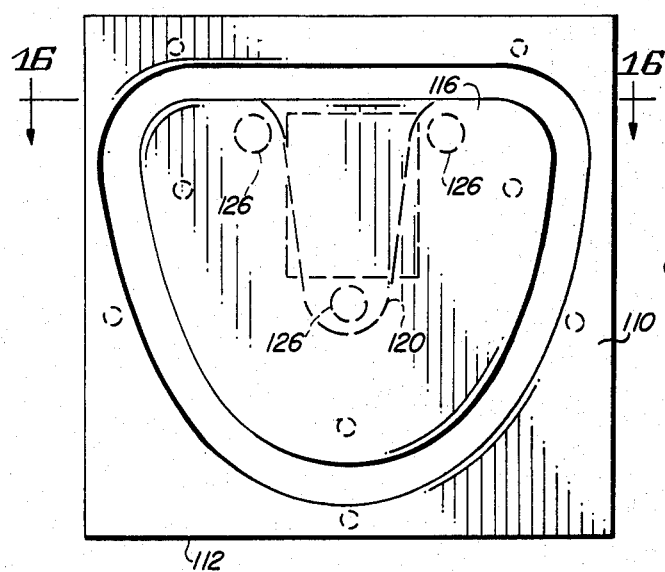
FIG-15
FIG-16
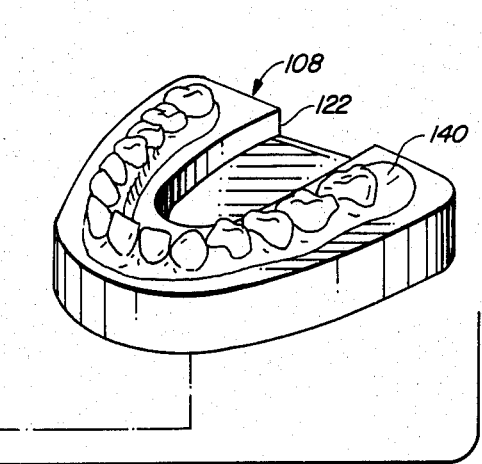
FIG-17

DENTAL MODEL BASE

This is a division of application, Ser. No. 230,330, filed Feb. 2, 1981 now U.S. Pat. No. 4,378,979.

The present invention relates to dental models and, more particularly, to molds and methods for using same to form the base of a dental model.

To accurately form and position false teeth or caps, a dentist normally makes a negative impression of the affected tooth or teeth. The negative impression may be partial, unilateral or bilateral, depending upon the extent of work to be done; the impression serves as a mold for developing a die of the patient's teeth. The negative impression is obtained by partially filling a tray with thermoplastic material. The filled tray is inserted within the patient's mouth such that the teeth and adjacent gums sink into and create a cavity within thermoplastic material. Shortly thereafter, the thermoplastic material will cure and retain an exact impression of the patient's teeth and adjacent gums. This is an essentially standard technique presently used by most dentists.

To form the die, a pourable casting stone, known as "pink stone" is poured into the negative impression up to at least the "margin" or base of the tooth. As described in more detail in U.S. Pat. No. 3,937,773, assigned to the present assignee, after the pink stone has been compacted to preclude voids and remove any air bubbles, a retainer and included guide pins is placed upon the surface of the pink stone such that the extending spade ends of the pins are sunk into the pink stone below the margin. Preferably, the degree of extension of the pins is such that the surface of the retainer rests upon the surface of the pink stone. After the pink stone is at least partially cured, wax or similar lubricant is swathed upon the surface of the pink stone.

Presently, the base for the dental mold is made by one of two methods. First, additional pourable hardenable stone, generally referred to as "yellow stone", is poured within the negative impression to cover the pink stone and the retainer with sufficient depth of yellow stone to form a solid base. After both the pink and the yellow stone have hardened, the tray and supported thermoplastic material is peeled away to leave a conventional dental model. Alternatively, a patty of yellow stone is formed upon a glass or other smooth surface. The partially or completely cured pink stone is placed thereupon such that the retainer extends into and is encapsulated by the yellow stone.

Either of the presently used methods for making the base of yellow stone requires substantial technician time to manually form the yellow stone into an initial shape. After it is cured, further time is required for cutting and grinding away excess yellow stone material. The time spent and material wasted necessarily adds to the cost of the dental model to the ultimate detriment of the patient.

In the presently used dental models, the mesial and distal cuts to be made through the line of demarcation between the pink and yellow stone must be made at an angle with respect to horizontal or the base surface in order to provide sufficient clearance for the saw end. The depth of cut necessitated by the cutting angle tends to weaken the structural integrity of the base resulting in either more fragile bases or bases which have to be substantially more thick than otherwise necessary to accommodate such weakening without breakage during normal handling.

Either of the above processes for making the bases of dental models tends to result in each base being somewhat unique and individualized. When the dental models are placed upon a dental articulator to perform work thereon, a substantial amount of time and expertise is necessary to properly attach and align the upper and lower coacting dental models to reproduce the relationship of the patient's jaws. The requisite time for aligning the dental models is exacerbated by the non-uniformity of the dental model base configurations and thicknesses and requires yet further time and effort to positionally orient each base upon its respective arm of the articulator and to attach the base to the arm.

It is therefore a primary object of the present invention to provide a standardized base for each type of dental model.

Another object of the present invention is to provide a base for a dental model which base includes a platform for supporting the tooth die.

Still another object of the present invention is to provide a base for a dental model which permits mesial and distal cuts to be made without weakening the structural integrity of the base.

Still another object of the present invention is to provide a standard sized base for a dental model and which base is positionally indexed with the arms of an articulator.

A further object of the present invention is to provide a method for making the base of a dental model, which base requires no manual shaping or finishing.

A yet further object of the present invention is to provide a method for forming a platform on the base of a dental model to support a tooth die.

A still further object of the present invention is to provide a method for forming right or left quadrant bases for dental models by reversing the position of an element of a mold.

A still further object of the present invention is to provide a flexible mold for making a standard sized base for a dental model having a raised platform to support a tooth die.

A still further object of the present invention is to provide a form for making flexible molds to mold uniformly shaped bases of dental models.

These and other objects of the present invention will become apparent to those skilled in the art as the description thereof proceeds.

The present invention may be described with greater specificity and clarity with reference to the following drawings in which:

FIG. 1 is an isometric view of a mold for making right or left quadrant bases for dental models;

FIG. 2 is a cross-sectional view taken along lines 2—2, as shown in FIG. 1;

FIG. 3 is an expanded view of the components shows in FIG. 1;

FIG. 4 is an isometric view of the bottom surface formed through use of the mold shown in FIG. 1;

FIG. 5 illustrates a reversably mountable element for making right or left quadrant bases;

FIG. 6 illustrates apparatus for forming a flexible mold to make the base of a dental model;

FIG. 7 is an exploded view of the apparatus shown in FIG. 6;

FIG. 8 illustrates an insert for the apparatus shown in FIG. 6;

FIG. 9 illustrates the flexible mold formed by the apparatus shown in FIG. 8;

FIG. 10 is a cross-sectional view taken along lines 10—10, as shown in FIG. 9;

FIG. 11 is an isometric view illustrating the dental model formed;

FIG. 12 is a cross-sectional view of a dental model formed;

FIG. 13 illustrates apparatus for forming a mold to make a unilateral base of a dental model;

FIG. 14 is a cross-sectional view taken along lines 14—14, as shown in FIG. 13;

FIG. 15 is a top view of the apparatus shown in FIG. 13;

FIG. 16 is a cross-sectional view taken along lines 16—16, as shown in FIG. 15; and FIG. 17 illustrates a flexible mold formed by the apparatus shown in FIG. 13 and the dental model made therefrom.

Referring to FIG. 1, there is shown a disassemblable mold 10 for making a right or left quadrant base 12 of a dental model 14 having a die 16 attached thereto. The mold includes a substructure 18 from which extend guide means, such as opposed channels 20, 22, a removable reversible insert 24 and a removable perimeter defining means such as wall 26 detachably attachable to the insert.

The components of mold 10 and their mutual cooperation will be described with joint reference to FIGS. 1-5. Normally, dental models must be located upon a dental articulator in order for a dentist or lab technician to perform work thereon and construct whatever prosthetic devices may be required to cure or alleviate a patient's dental problem. To standardize the attachment location and orientation of the dental model, indexing means, such as depressions 28, are formed in bottom surface 30 of base 12 by nipples 29 extending upwardly from the surface of substructure 18. Thereby, each base formed by mold 10 will have a uniformly positioned indexing means for cooperative engagement with complementary indexing means permanently attached to an arm of an articulator. To avoid the need for mastic or other adhesive substances presently used to maintain a dental model attached to the arm of an articulator, a magnet 32 is formed as part of the bottom of base 12. The magnet cooperates with a commensurately located metal plate upon an arm of the articulator. Alternatively, the locations of the magnet and plate may be reversed. Thereby, the dental model is maintained in engagement with the arm of an articulator by magnet 32 and indexed with respect thereto by means of depressions 28. The location of magnet 32 in base 12 is predetermined by delineation 34 or similar physical key means upon the surface of substructure 18.

Insert 24 slidably cooperates with channels 20 and 22 to removably locate the insert upon substructure 18. The insert includes a wall 36 of which lower wall 38 defines a part of the perimeter of base 12. A plate 40 extends laterally from wall 36 and defines a void in the base to be formed. The configuration of wall 36 and the location of plate 40 thereon is such that the insert may be brought into slidable engagement with channels 20 and 22 to reorient the plate from right to left and vice versa whereby the void formed may be reversed in position with respect to base 12.

Wall 26 includes ends 42 and 44, which ends are slidably engagable with slots 46, 48 disposed in wall 36. The interior surface of wall 26 defines the perimeter wall of base 12. It may be noted that curved wall 50 of plate 40 is commensurate in curvature with the interior surface of wall 26 and is located adjacent thereto upon assembly.

To form base 12 in mold 10, a magnet 32 is placed within delineations 34. Insert 24 is seated within channels 20 and 22 whereafter wall 26 is brought into retaining engagement with respective ones of slots 46 and 48. Yellow stone is poured into the resulting cavity. The yellow stone will flow beneath plate 40, as illustrated in FIG. 2, around and about magnet 32 and up to a level coincident with the top of wall 26 and the top surface of plate 40. A screed or the like may be employed to obtain a level top surface of the yellow stone. Before the yellow stone sets, a tooth die 16, having a plurality of dowels or pins 17 depending therefrom is placed upon the uncured exposed surface of the base. Preferably, the extending part of pins 17 is commensurate in length with the thickness of base 12, as shown in FIG. 2. After curing, wall 26 and insert 24 are disassembled and the base may be lifted off substructure 18. The resulting base will have a platform 13 which platform supports die 16 in either a right or left quadrant, depending upon the orientation of insert 24.

To sever a model tooth 54 (see FIG. 3) mesial and distal saw cuts 56, 58 are made through die 16 to a point just below the line of demarcation 60. Further depth of cut is unnecessary as platform 13 raises the saw blade sufficiently above the remaining part of the base to prevent interference with the end of the saw blade (see FIG. 12). As pointed out above, in presently made dental models, the saw cut has to be made at a substantial angle to accommodate the saw blade end. An indent 31 may be formed in the bottom surface 30 to aid in pushing upon pins 17 to remove a model tooth.

Base 12, when removed from within mold 10, is of a minimum perimeter commensurate with the sides of die 16. It is smooth surfaced as a result of the surface smoothness of the various components of the mold and is ready for use without further finishing by technicians. Additionally, the die is indexed and includes means for adhering it to the arm of an articulator without further work by technicians. It is to be noted, that magnet 32 will be replaced by a steel plate or the like which will be magnetically coupled to a magnet located in the arm of the articulator.

Referring jointly to FIGS. 6–12 there is shown apparatus 62 for constructing a flexible mold 80 for a base 90 of a dental model. The apparatus includes a substructure 64 supporting a cast 66. The cast has a void 68 extending through the cast and commensurate in planform with the configuration of the exterior dimensions of mold 80 to be formed. An insert 70, representative of the exact configuration of base 90 to be developed from the mold produced by apparatus 62, is attached to platform 64 by bolts or other mechanical means and located generally central to void 68. Bottom surface 72 of the insert includes depressions 74 for forming nipples in the mold, which nipples when reproduced by the base to be molded serve as index means, as described above. Additionally, a raised rectangular segment 76 extends upwardly from surface 72 to form a recess in the base to be molded, which recess is used to seat a magnet or a steel plate.

As shown in greater detail in FIG. 8, the insert includes a raised part 78 commensurate in configuration with the platform of the base to be formed. Threaded cavities 81 extend into raised part 78 to secure insert 70 by bolts or other means to substructure 64.

FIGS. 9 and 10 illustrate flexible mold 80 which can be produced from apparatus 62 by pouring a curable rubber compound into void 68 of apparatus 62 and allowing it to cure. An example of a suitable rubber compound is sold by the Friedheim Tool Supply Company under the mark Jofre. The mold includes nipples 82 which will form depressions in the base to be molded and serve as index means on attachment of the base to an arm of an articulator. A recess 84 is sized to receive a steel plate or magnet which will locate and retain in place the opposite element to be lodged within the base to be formed. An overhang 86 serves the same function as insert 40 of mold 10, as shown in FIGS. 1 and 2; that is, it, in combination with side wall 88, defines the outline of the platform to be formed as part of the base.

Base 90 formable from mold 80 is illustrated in FIGS. 11 and 12. It includes a raised part referred to as platform 92, which platform supports tooth die 94. Tapered pins 96 or constant diameter pins 17 (as shown in FIG. 2) may be used to key the die to the base. As particularly illustrated in FIG. 12, a saw blade 98 can be held and maintained horizontal to make the mesial and distal cuts through die 94 to a point just below line of demarcation 100. Thereafter, an individual model tooth 102 or a section of model teeth can be replaceably removed for working on the dental model.

In operation, after formation of die 94, pourable yellow stone is poured into mold 80 to a level even with the top surface of the mold and assuming that either a magnet or a steel plate has already been inserted and positioned within the mold. Die 94 is thereafter placed upon the exposed surface of yellow stone intermediate the perimeter of overhang 86 and side wall 88, as illustrated in FIGS. 11 and 12. Priorly, a release compound is placed upon the exposed surface of yellow stone or upon the base of the die. After curing of the yellow stone, base 90 is formed. The base will have disposed therein the index means as a result of the depressions created by nipples 82 and includes a magnet or a steel plate for removably attaching the base to an arm of an articulator. Removal of the base from within the mold is accomplished by non-destructively distending the mold walls to release the base.

Apparatus 160 shown in FIGS. 13, 14, 15 and 16 is employed to form a flexible mold for making a full base 108 (see FIG. 17) for a dental model. The apparatus includes a substructure 110 supporting a cast 112. The cast includes a void 114 commensurate in size and planform with the exterior dimensions of the mold to be formed. An insert 116 is disposed within void 114 and attached to substructure 110. The insert is commensurate in configuration with the configuration of the base to be formed. The insert includes a perimeter wall 118 to define the perimeter of the base and the exterior perimeter of platform 122 and a depression 120 commensurate in depth, width and height of the interior dimensions of the platform of base 108 (see FIG. 17). A raised rectangular segment 124 develops a recess in the mold to receive either a steel plate or a magnet. Depressions 126 form nipples 136 in the mold which result in depressions in base 108 which serve as index means for attaching the dental model to the arm of an articulator. Bolt means, or the like, engaging threaded cavities are employed to secure cast 112 and insert 116 to substructure 110.

By pouring a curable rubber compound into void 114 of apparatus 106, a flexible mold 130, shown in FIG. 17, is produced. The mold includes an inner wall 132 for defining the perimeter of the base, a tongue or overhang 134 for defining the height and width of platform 122, nipples 136 for producing index means in the bottom surface of the base and either an imbedded steel plate or magnet 138 for maintaining in place the base with a magnetically complementary element. After the yellow stone has been poured within mold 130, die 140 is located thereupon, as described in detail above. Upon curing of the base, it may be removed from within mold 130 by non-destructively distending the mold walls to release the cured dental model.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

I claim:

1. A base for use in a dental model to support a tooth die, said base comprising in combination:
   (a) a body, said body including a planar top surface, a planar bottom surface essentially parallel with said top surface and a perimeter surface interconnecting said top and bottom surfaces, said perimeter surface being defined by a rear portion, extending between two rear corners and two converging symmetric convex sides extending from said corners and joining each other at a centrally located point at the front of said body; and
   (b) a platform formed upon and extending upwardly from said top surface of said body a distance less than the height of said body for supporting the bottom surface of the tooth die, said platform including an outer marginal edge defined by an upward extension of said perimeter surface attendant a part of said rear portion, said two rear corners and said convex sides and an inner marginal edge defining an inner recessed portion, said outer and inner marginal edges defining an approximately uniform width therebetween, said inner recessed portion being coincident with a part of said top surface of said body and including concave sides converging from said rear portion toward but short of the front point of said body and depending from said inner marginal edge.

2. The base as set forth in claim 1 wherein said convex and concave sides are essentially perpendicular to said top surface.

3. The base as set forth in claim 2 wherein said convex and concave sides are essentially impervious.

4. A base for use in a dental model to support the bottom surface of a tooth die, said base comprising in combination:
   (a) a body, said body including a planar top surface, a planar bottom surface essentially parallel with said top surface and a perimeter surface interconnecting said bottom surface with a portion of said top surface, said perimeter surface being defined by a rear portion extending between a pair of rear corners, one side joined to one of said rear corners and a convex side extending from another of said corners toward the front of said base to join said one side at a point offset to one side of the planform major axis of said base; and
   (b) a platform, formed upon and extending upwardly from said top surface of said body a distance less than the height of said body for supporting the bottom surface of the tooth die said platform including an outer marginal edge defined by an upward extension of said convex side and an inner concave marginal edge defining a recessed portion, said outer and inner marginal edges defining an approximately uniform width therebetween, a wall depending from said inner marginal edge, said recessed portion being coincident with a part of said top surface of said body and defined by a segment of said rear portion, said wall and said convex side.

5. The base as set forth in claim 4 wherein said convex side and said wall are essentially impervious.

* * * * *